United States Patent
Eckman

(10) Patent No.: US 8,282,661 B2
(45) Date of Patent: Oct. 9, 2012

(54) MULTI-BLADE CURETTE TOOL

(75) Inventor: Walter W. Eckman, Tupelo, MS (US)

(73) Assignee: Concept Matrix, LLC, Orlando, FL (US)

( * ) Notice: Subject to any disclaimer, the term of this patent is extended or adjusted under 35 U.S.C. 154(b) by 628 days.

(21) Appl. No.: 11/422,460

(22) Filed: Jun. 6, 2006

(65) Prior Publication Data

US 2006/0276816 A1 Dec. 7, 2006

Related U.S. Application Data

(60) Provisional application No. 60/687,840, filed on Jun. 6, 2005.

(51) Int. Cl.
*A61B 17/22* (2006.01)
*A61D 1/02* (2006.01)

(52) U.S. Cl. ........... 606/160; 606/1; 606/53; 606/79; 606/80; 606/167; 606/180; 600/570; 433/165; 407/30; 408/22

(58) Field of Classification Search .......... 606/1, 53, 606/79, 80, 160, 167, 180; 600/570; 623/17.11, 623/17.16; 407/30; 408/22; 30/500; 433/165
See application file for complete search history.

(56) References Cited

U.S. PATENT DOCUMENTS

| 651,395 | A | * | 6/1900 | Stapp | 606/160 |
| 706,013 | A | * | 8/1902 | Boyce | 433/165 |
| 4,757,826 | A | * | 7/1988 | Abdulhay | 600/570 |
| 5,250,061 | A | * | 10/1993 | Michelson | 606/160 |
| 6,726,690 | B2 | * | 4/2004 | Eckman | 606/79 |
| 2005/0107816 | A1 | * | 5/2005 | Pingleton et al. | 606/185 |

OTHER PUBLICATIONS

KMEDIC Catalog; Curettes; 3 pages depicting various styles of Curettes (date unknown).
U.S. Appl. No. 29/247,217, filed Jun. 2006, Eckman.

* cited by examiner

*Primary Examiner* — Gary Jackson
*Assistant Examiner* — Kevin Everage
(74) *Attorney, Agent, or Firm* — Panitch Schwarze Belisario & Nadel LLP

(57) ABSTRACT

A multi-blade curette tool for use in spinal surgery. The curette tool includes an elongated member having a first end and a second end. A handle is disposed at the first end. A curette head is disposed at the second end. The curette head is generally tapered toward the first end and the second end. The curette head includes a convexly-shaped and generally tapered nose portion, a base portion, and a plurality of blades. Each blade extends between the base portion and the nose portion, and each of the plurality of blades is provided with at least one cutting element. A drive stem connects the handle and the curette head. At least one cutting element of each blade is adapted to remove spinal disk material upon rotation of the curette tool in at least one direction.

12 Claims, 6 Drawing Sheets

US 8,282,661 B2

MULTI-BLADE CURETTE TOOL

CROSS REFERENCE TO RELATED APPLICATIONS

This application claims priority to U.S. Provisional Application No. 60/687,840, filed Jun. 6, 2005, entitled "Multi-Blade Curette with Convex Profile."

BACKGROUND OF THE INVENTION

Embodiments of the present invention relate to a curette used in spinal surgery on animals and humans, and more particularly to a multi-blade curette tool for use in spinal surgery.

It is known to use curettes in surgical and other medical procedures to debride or clean spaces or cavities in the body (e.g., ears, uterus, sinuses, cavities within skeletal structures, and spinal disk spaces). Early curettes were simple spoon-like cups. It is known to include an angled section in such spoon-like curettes to facilitate the curetting process when an opening through which the curette is inserted is smaller than the cavity to be cleaned. Ring curettes are also known. Ring curettes have two blades which contact walls of the cavity. Ring curettes allow cleaning of spaces at greater depths within the body, as ring curettes typically require less tilting than the spoon-like curettes. In operation, ring curettes do require some tilting, which leads to uneven pressure on the cavity walls. Further, ring curettes make contact at one time with only a small portion of the entire surface to be cleaned. The curetting process using known curettes tends to be time-consuming and relatively inefficient. Furthermore, ring curettes require an opening into the cavity to be nearly as large as the ring formed by the curette blades.

In general, there is a need for a more efficient curette. With the advent of minimally invasive spine surgery, there is a particular need for a more efficient and effective curette for cleaning out central portions of the disk space.

BRIEF SUMMARY OF THE INVENTION

Briefly stated, embodiments of the present invention are directed to a multi-blade curette tool for use in spinal surgery. The curette tool comprises an elongated member having a first end and a second end. A handle is disposed at the first end. A curette head is disposed at the second end. The curette head is generally tapered toward the first end and the second end. The curette head includes a convexly-shaped and generally tapered nose portion, a base portion, and a plurality of blades. Each blade extends between the base portion and the nose portion, and each of the plurality of blades is provided with at least one cutting element. A drive stem connects the handle and the curette head. The at least one cutting element of each blade is adapted to remove spinal disk material upon rotation of the curette tool in at least one direction.

BRIEF DESCRIPTION OF THE SEVERAL VIEWS OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
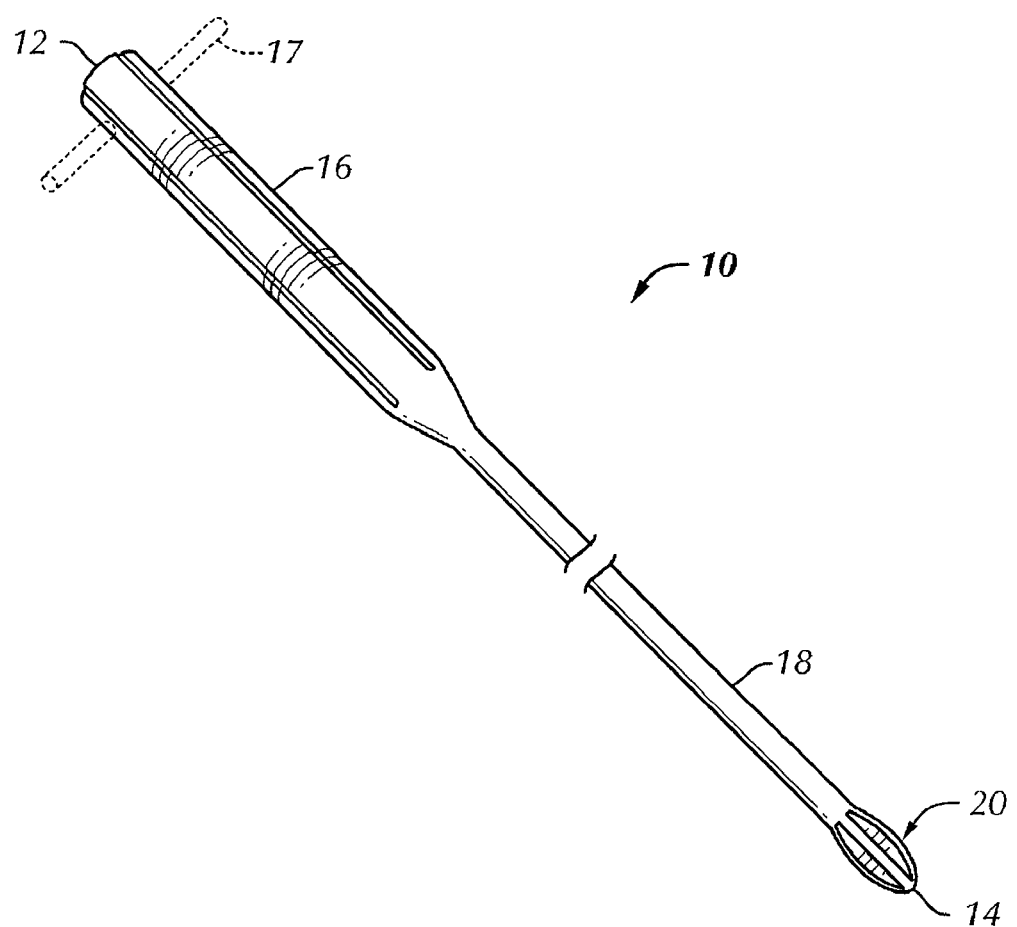
FIG. 1 is a plan view of a multi-blade curette tool in accordance with a preferred embodiment of the present invention.

Certain terminology is used in the following description for convenience only and is not limiting. The words "right", "left", "lower", and "upper" designate directions in the drawing to which reference is made. The words "inwardly" and "outwardly" refer direction toward and away from, respectively, the geometric center of the multi-blade curette and designated parts thereof. The terminology includes the words above specifically mentioned, derivatives thereof and words of similar import. Additionally, the word "a", as used in the claims and in the corresponding portions of the specification, means "at least one."

Referring to the drawings in detail, wherein like reference numerals indicate like elements throughout, and with initial reference to FIG. 1, there is shown a multi-blade curette tool 10 (or "curette 10") in accordance with a preferred embodiment of the present invention. The curette 10 is adapted for use in spinal surgery. The curette 10 comprises an elongated member having a first or proximal end 12 and a second or distal end 14. A handle 16 is disposed at the first end 12, while a curette head 20 (or "head 20") is disposed at the second end 14. A drive stem 18 connects the handle 16 and the head 20. The curette head 20 is generally convexly tapered on the outer surface. Optionally, there may be a proximal rod handle 17 (shown in phantom in FIG. 1) for giving leverage during turning and removal of the curette 10. The proximal rod handle 17 may be fixed to the handle 16, hingedly attached to the handle 16 or releasable attached to the handle 16.

With reference to FIGS. 2-5, the head 20 includes a nose portion 24 (or "nose 24") proximate the elongated member second end 14 and a base portion 22 (or "base 22") intermediate the elongated member first and second ends 12 and 14. The curette head 20 is generally tapered toward the second end 14 to facilitate distraction and entry into the space between vertebral bodies, and the curette head 20 is also generally tapered toward the drive stem 18 so as to facilitate removal from the space. T he overall shape of the curette head 20 is similar to an American football or an ellipsoid truncated at the base 22 by the drive stem 18. The curette head 20 is generally symmetrical along a longitudinal axis defined between the second end 14 and the first end 12. The head 20 further includes a plurality of blades 26, i.e., two or more blades 26. Preferably, there are three or more blades 26, which in combination are sized, shaped and spaced to balance or equalize the pressure exerted against the surfaces of the opposing vertebral bodies while the end plate disk material, cartilage and/or bone is curetted. Each blade 26 extends between the base portion 22 and the nose portion 24. As discussed below, multiple embodiments of the blades 26 are disclosed herein. Each blade 26 is provided at least one cutting element 28. Each blade 26 is provided with an outer face 36. As discussed below, multiple embodiments of the cutting elements 28 adapted for use with one or more of the embodiments of the blades 26 are also disclosed herein, and each of the multiple embodiments of the cutting elements 28 may be used alone or in combination with any of the various embodiments of the head 20.

Figure 2:
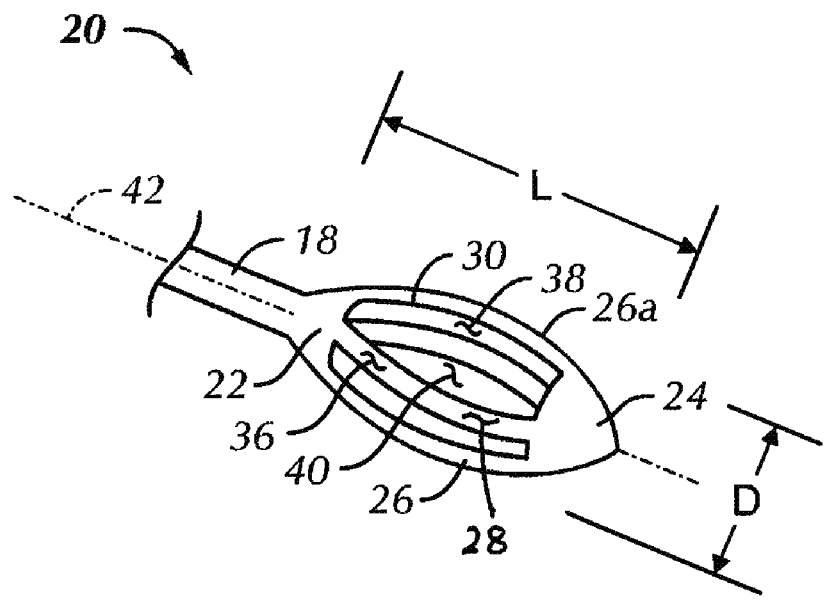
FIG. 2 is a side perspective view of a head portion of the curette tool of FIG. 1, shown having a first style of blade and a continuous knife edge cutting element.

The head 20 is sized and shaped to fit within an intervertebral space. Thus, the head 20 preferably has a tubular, convex shape. With reference to FIG. 2, the head 20 has a maximum diameter D, preferably in the range of 6 to 15 mm, at an axial location intermediate the base 22 and the nose 24. The head 20 has a length L, preferably in the range of 10 to 30 mm, along a longitudinal axis 42. An outer profile of the head 20 is characterized by a relatively gradual slope, such that the diameter of the head 20 preferably changes no more than about 2 mm for every 1 mm change in length. The nose 24 is preferably relatively small, for example, less than 2.5 mm in diameter over the terminal 1 mm of the second end 14 along the longitudinal axis 42 or approximately 5-20% of the maximum diameter D of the head 20. The taper and slope of the second or distal end 14 of the head 20 permit the head 20 to be at least partially self-distracting in some applications. The head 20 may be dimensioned in accordance with the requirements of specific applications, and other dimensional characteristics of the head 20 are included within the scope of this invention.

The head 20 is preferably fixedly connected to the drive stem 18, but the head 20 may be releasably coupled to the drive stem 18 by a detent, set-screw, threaded or counter-threaded connection or the like. The head 20 may be formed integrally and unitarily with a remainder of the curette tool 10. The outer radial extent of the drive stem 18 is preferably minimized to reduce the degree to which the drive stem 18 obscures the surgeon's view of the head 20 when the head 20 is inserted into a patient.

Figure 3:
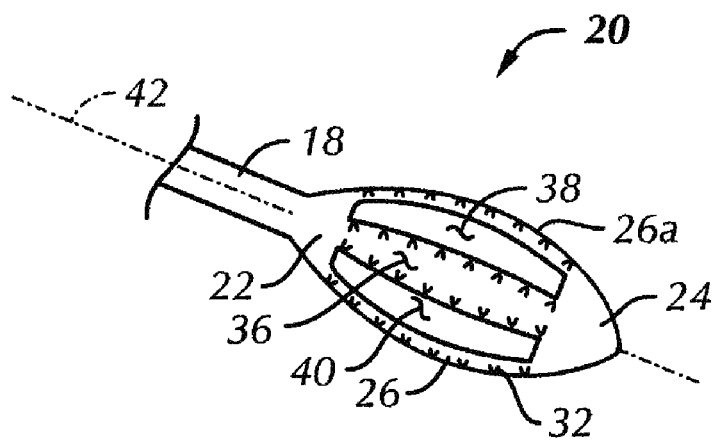
FIG. 3 is a side perspective view of the head portion of the curette tool of FIG. 1, shown having the first style of blade and a plurality of spike cutting elements or rasp-like projections.
Figure 4:
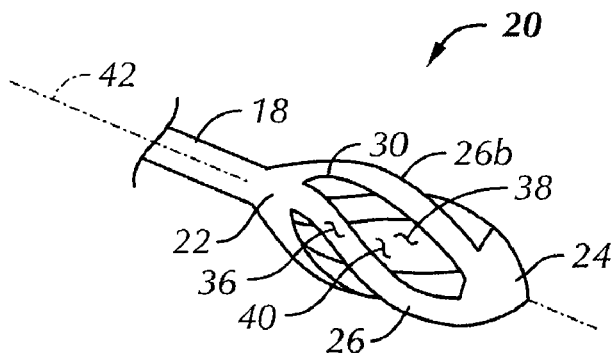
FIG. 4 is a side perspective view of the head portion of the curette tool of FIG. 1, shown having a second style of blade and the continuous knife edge cutting element.
Figure 5:
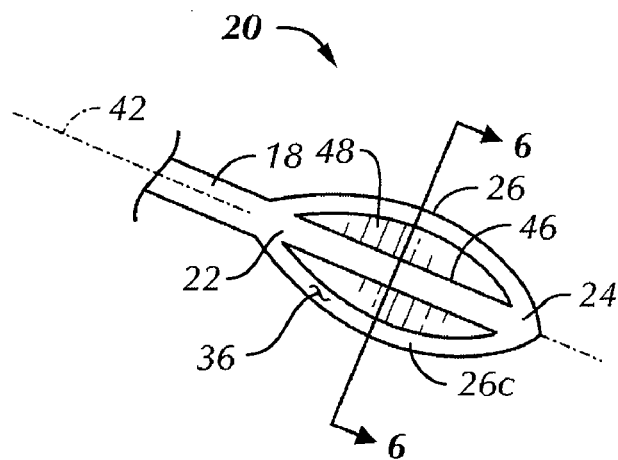
FIG. 5 is a side elevational view of the head portion of the curette tool of FIG. 1, shown having a third style of blade and the continuous knife edge cutting element.
Figure 6:
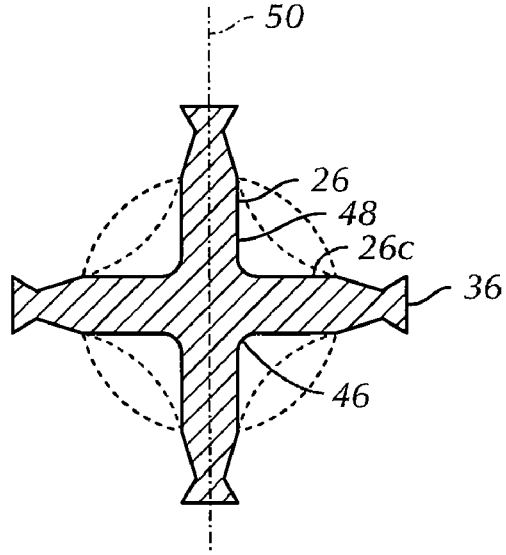
FIG. 6 is a cross-sectional view of the head portion of FIG. 5 taken along line 6-6.

With reference now to FIGS. 2-6, preferably at least three blades 26 are provided. Additional blades 26 may be provided, such as the four blades 26 illustrated. A first embodiment blade 26a is illustrated in FIGS. 2 and 3, while a second embodiment blade 26b is illustrated in FIG. 4, and a third embodiment blade 26c is illustrated in FIGS. 5 and 6.

With particular reference to FIGS. 2 and 3, the first embodiment blade 26a is an elongated member having a first end connected between the base 22 and the nose 24. The first embodiment blade 26a may be unsupported from the interior volume 40 as best shown in cross-section in FIG. 7. Alternately, the first embodiment blade 26a may be supported by cross-bracing or a nearly solid fill within the interior volume 40 such that indentations or slight recesses are left in spaces or openings 38 between blades 26a. The first embodiment blade 26a generally extends between the base 22 and the nose 24, or from the base 22 to the nose 24, in a generally arcuate manner in a direction generally along the central longitudinal axis 42 of the curette head 20.

With particular reference to FIG. 4, the second embodiment blade 26b is also an elongated member supported only at its first and second ends by the base 22 and nose 24, respectively. However, the second embodiment blade 26b extends between the blade first end and the blade second end in a direction which is not parallel to the central longitudinal axis 42 of the curette head 20. That is, the second embodiment blades 26b are "twisted" along the longitudinal axis 42. The twisted blade feature of the second embodiment blade 26b may facilitate entry of the curette head 20 through an opening into a cavity to be cleaned by providing a thread-like or screw-like action.

The first and second embodiment blades 26a, 26b form a central cavity or interior volume 40 within the curette head 20. Blade openings 38 are provided between the blades 26a, 26b, providing access to the interior volume 40.

With particular reference to FIGS. 5 and 6, the third embodiment blade 26c is preferably a plate-like member extending radially from a completely solid central core 46 of the curette head 20. The third embodiment blade 26c is a continuous member having a first end connected to the base 22 and a second end connected to the nose 24. An interior portion 48 of the third embodiment blade 26c is connected to the central core 46. It will be appreciated that the third embodiment blade 26c is a structurally stiffer construction than that provided by the first and second embodiment blades 26a, 26b. The third embodiment blade 26c is preferably planar as illustrated in FIGS. 5 and 6, having a central longitudinal plane 50 extending radially from the central core 46. Alternatively, the third embodiment blade 26c may have other internal support structure configurations as shown in phantom in FIG. 6 to facilitate fabrication and/or to facilitate cleaning during use. Alternatively, the third embodiment blade 26c could be non-planar (that is, curved), for example similar in cross-section (taken perpendicular to the radial dimension of the blade) to the second embodiment blade 26b. It is preferred that the curette head 20 includes at least two imaginary planes that extend through and include the longitudinal axis 42 of the curette 10 and the curette head 20. It is preferred that each imaginary plane extends radially outwardly from the longitudinal axis 42 and that the at least two imaginary planes define an angle of less than 180° and greater than 0° therebetween. Each imaginary plane preferably divides each of the nose portion 24 and the base portion 22 into two generally equal halves. It is also preferred that at least one blade of the plurality of blades 26c extends within one of the at least two imaginary planes and at least one other blade of the plurality of blades 26c extends within another one of the at least two imaginary planes.

Figure 7:
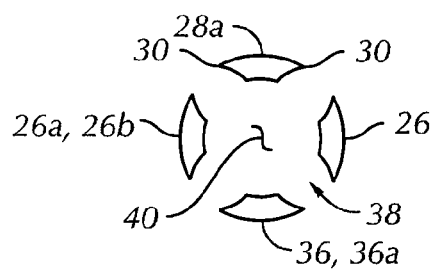
FIG. 7 is a partial cross-sectional view of the curette head of FIGS. 2 and 4, showing a first embodiment cutting element arrangement especially suitable for use with either the first or second style blades.

The blades 26 can be provided with various types of cutting elements 28. Any of the cutting elements depicted in FIGS. 7-19 can be used alone or in combination with any of the blade embodiments 26a-26c, as well as any other known or contemplated cutting element 28. With reference to FIG. 7, a first embodiment cutting element arrangement 28a includes two opposing sharpened, knife-like edges 30 extending generally the length of the blade 26, that is, from the blade first end to the blade second end. As two opposing edges are provided, the first embodiment cutting element arrangement 28a is capable of cutting and removing disk material when the tool is rotated (about the longitudinal axis 42) in either a clockwise or a counterclockwise direction. The blade outer surface 36 associated with the first embodiment cutting element arrangement 28a is preferably radiused to define the tapered outer diameter of the curette head 20, forming a radiused outer face 36a. The first embodiment cutting element arrangement 28a is particularly well-suited for use with either the first embodiment blade 26a or the second embodiment blade 26b. The knife edges 30 of the cutting element 28a are shown in FIG. 7 as being generally within an outermost radius defined by the outer face 36a. Alternately, the knife edges 30 may be slightly curved or shaped to extend beyond the radius defined by the outer face 36a.

Figure 8:
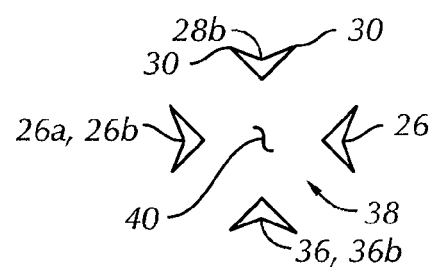
FIG. 8 is a partial cross-sectional view of the curette head of FIGS. 2 and 4, showing a second embodiment cutting element arrangement especially suitable for use with either the first or second style blades.

With reference now to FIG. 8, a second embodiment cutting element arrangement 28b is similar to the first embodiment cutting element arrangement 28a in that it provides bi-directional cutting, by providing two continuous opposing sharpened knife edges 30 generally extending from the blade first end to the blade second end. The second embodiment cutting element arrangement 28b is similarly suitable for use with either the first embodiment blade 26a or the second embodiment blade 26b. The second embodiment cutting element arrangement 28b differs in that a central portion of the blade outer surface 36 may be recessed and/or flat relative to the blade edges, forming a recessed outer face 36b such that the blade edges extend beyond the radius defined by outer face 36b. The edges 30 are positioned to extend radially beyond a remainder of the outer face 36b by a predetermined amount. The radial position of the cutting edges 30 may be adjusted to control the level of cutting or abrasion provided by the curette head 20. The outer face 36b of the blades could be straight walled instead of dimpled similar to the outer face 36c of the blade 26 shown in FIG. 9.

Figure 9:
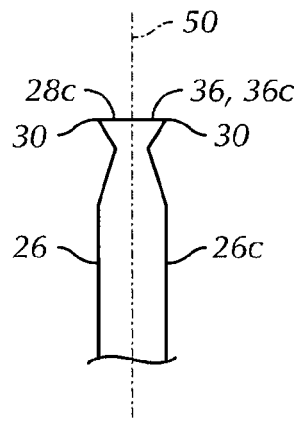
FIG. 9 is a partial cross-sectional view of the curette head of FIGS. 5 and 6, showing a third embodiment cutting element arrangement especially suitable for use with the third style blade.

With reference now to FIG. 9, a third embodiment cutting element arrangement 28c, like the first and second cutting element arrangements 28a, 28b, provides two opposing sharpened knife-like edges 30, and is thus also adapted for bi-directional cutting. The third embodiment cutting element arrangement 28c is well-suited for use with the third embodiment blade 26c. The blade outer surface 36 preferably associated with the third embodiment cutting element arrangement 28c is a flat outer face 36c. Each sharpened edge 30 extends tangentially to the blade outer surface 36 throughout the length of the curette head 20. As shown in FIGS. 6 and 9, at least a portion of each sidewall of each blade 26c of the third embodiment extends at an angle of less than 90° from the blade outer surface 36.

Figure 10:
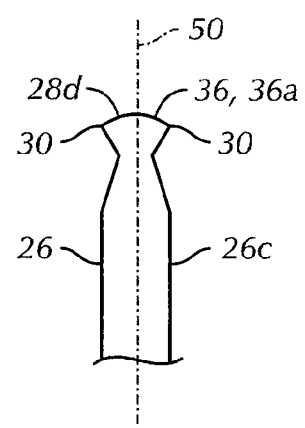
FIG. 10 is a partial cross-sectional view of the curette head of FIGS. 5 and 6, showing a fourth embodiment cutting element arrangement especially suitable for use with the third style blade.

With reference now to FIG. 10, a fourth embodiment cutting element arrangement 28d also provides two opposing sharpened knife-like edges 30, and is thus also adapted for bi-directional cutting. The fourth embodiment cutting element arrangement 28d is also well-suited for use with the third embodiment blade 26c. The blade outer surface 36 preferably associated with the fourth embodiment cutting element arrangement 28d is the radiused face 36a.

Figure 11:
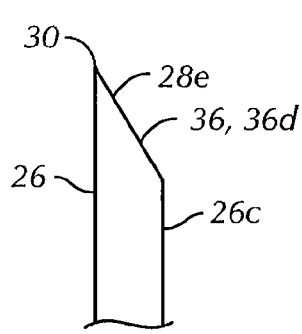
FIG. 11 is a partial cross-sectional view of the curette head of FIGS. 5 and 6, showing a fifth embodiment cutting element arrangement especially suitable for use with the third style blade.

With reference now to FIG. 11, a fifth embodiment cutting element arrangement 28e provides a single sharpened knife-like edge 30. The fifth embodiment cutting element arrangement 28e is especially suitable for use with the third embodiment blade 26c. The blade outer surface 36 preferably associated with the fifth embodiment cutting element arrangement 28e is a flat, angled outer face 36d. The single sharpened knife-like edge 30 may be centered or off-centered as shown in FIG. 11.

Figure 12:
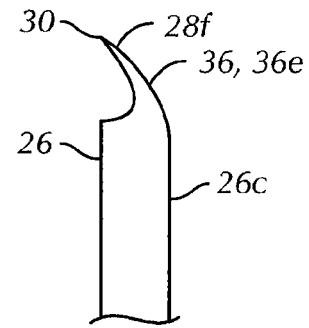
FIG. 12 is a partial cross-sectional view of the curette head of FIGS. 5 and 6, showing a sixth embodiment cutting element arrangement especially suitable for use with the third style blade.
Figure 13:
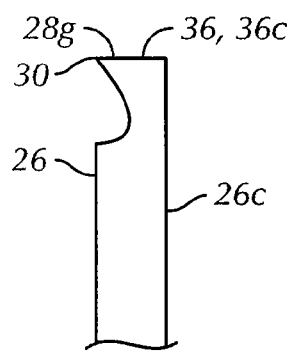
FIG. 13 is a partial cross-sectional view of the curette head of FIGS. 5 and 6, showing a seventh embodiment cutting element arrangement especially suitable for use with the third style blade.

With reference now to FIGS. 12 and 13, sixth and seventh embodiment cutting element arrangements 28f, 28g, respectively, also provide but a single sharpened knife-like edge 30. Both the sixth and seventh embodiment cutting element arrangements 28f and 28g are especially suitable for use with the third embodiment blade 26c. The blade outer surface 36 preferably associated with the sixth embodiment cutting element arrangement 28f is non-symmetrically radiused (that is, provided with a radius not matching the outer circumference of the curette head 20) outer face 36e. The blade outer surface 36 preferably associated with the seventh embodiment cutting element arrangement 28g is the flat outer face 36c.

Figure 14:
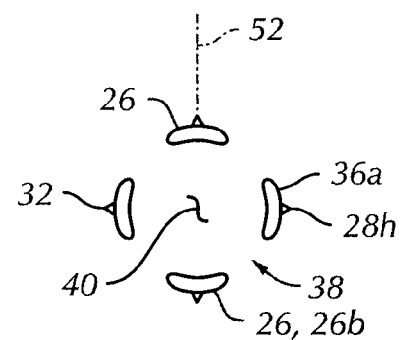
FIG. 14 is a partial cross-sectional view of the curette head of FIG. 3, showing an eighth embodiment cutting element arrangement suitable for use with the first, second, or third style blades.
Figure 15:
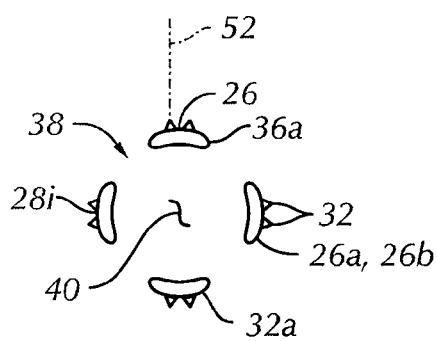
FIG. 15 is a partial cross-sectional view of the curette head of FIG. 3, showing a ninth embodiment cutting element arrangement suitable for use with the first, second, or third style blades.
Figure 16:
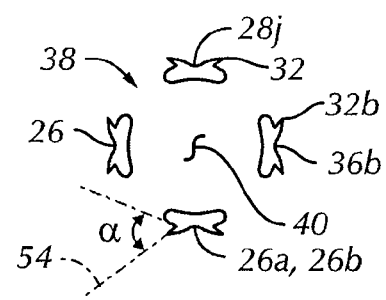
FIG. 16 is a partial cross-sectional view of the curette head of FIG. 3, showing a tenth embodiment cutting element arrangement suitable for use with the first, second, or third style blades.

With particular reference now to FIGS. 14-16, eighth, ninth, and tenth embodiment cutting element arrangements 28h, 28i, and 28j, respectively, each include a plurality of spikes or rasp-like projections 32. The eighth, ninth, and tenth embodiment cutting element arrangements 28h, 28i, and 28j are especially well-suited for use with any of the first, second, and third blade embodiments 26a-26c. The eighth and ninth embodiment cutting element arrangements 28h and 28i are provided with radially-extending spikes 32a, each having a central axis 52 extending radially (that is, substantially perpendicularly) from the blade outer surface 36. The tenth embodiment cutting element arrangement 28j is provided with angled spikes 32b, each having a central axis 54 extending from the blade outer surface 36 at an acute angle α, such that the angled spikes 32b bite more aggressively when rotated into cutting contact with disk material, cartilage and/or bone as compared to the radially-projecting spikes 32a.

Figure 17:
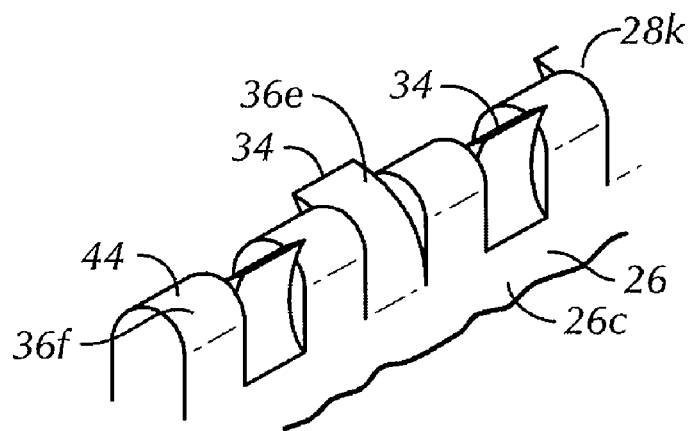
FIG. 17 is a partial perspective view of the curette head of FIGS. 5 and 6, showing an eleventh embodiment cutting element arrangement especially suitable for use with the third style blade.
Figure 18:
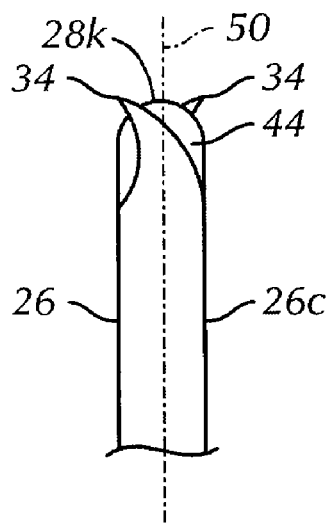
FIG. 18 is a partial cross-sectional view of the curette head of FIGS. 5 and 17, showing the eleventh embodiment cutting element arrangement.
Figure 19:
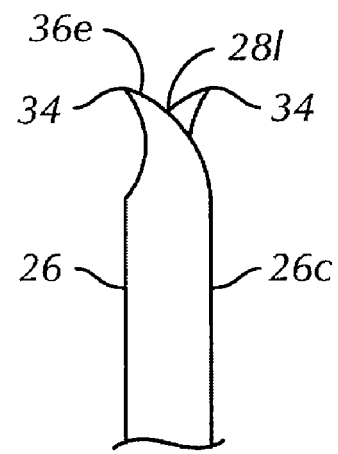
FIG. 19 is a partial cross-sectional view of the curette head of FIGS. 5 and 6, showing a twelfth embodiment cutting element arrangement especially suitable for use with the third style blade.

With reference now to FIGS. 17-19, eleventh and twelfth embodiment cutting element arrangements 28k and 28l, respectively, each include a plurality of alternating opposed teeth 34. The eleventh and twelfth embodiment cutting element arrangements 28k and 28l are especially well-suited for use with the third blade embodiment 26c. The teeth 34 of the eleventh and twelfth embodiment cutting element arrangements 28k and 28l are arranged in an alternating manner such that a first tooth 34 is adapted to remove disk material, cartilage and/or bone when the tool 10 is rotated in a first direction, and an adjacent tooth 34 is adapted to remove disk material, cartilage and/or bone when the tool 10 is rotated in a second direction. In the eleventh embodiment cutting element arrangement 28k, adjacent teeth 34 are separated by spacer members 44. The spacer members 44 are blunt and recessed relative to the tooth cutting edges, and do not perform a cutting function. The teeth 34 could be centered, off-centered, straight or curved, and if the teeth 34 are curved, adjacent teeth 34 can be alternately facing in opposite directions for bi-directional cutting as shown in FIGS. 17-19.

The first through seventh embodiment cutting element arrangements 28a-28g are particularly well-suited for cleaning of a cavity. The eighth through twelfth embodiment cutting element arrangements 28h-28l are particularly well-suited for more aggressive removal of material from walls of the cavity. But, the various embodiment cutting elements 28a-28l may be suited for either application, alone or in combinations thereof.

In use, the surgeon would typically employ the curette tool 10 provided with preferably one of the first through seventh embodiment cutting elements 28a-28g when performing a cleaning function in a cavity and the curette tool 10 provided with preferably one of the eighth through twelfth embodiment cutting elements 28h-28l when performing a more aggressive abrading function. The small nose 24, and the gradual sloping profile of the curette head 20 permit the curette head 20 to be relatively easily inserted into a cavity to be cleaned. In the context of spinal surgery, the curette tool 10 can be inserted into a disk space though a small opening in the annular ligaments with the curette tool 10 creating its own distraction of the adjacent vertebral body peripheral bone edges. Rotation of the handle 16 and consequently of the curette head 20 causes the blades 26 and cutting elements 28 to engage the cavity wall, removing cavity wall material and debris.

The curette tool 10 is preferably fabricated from oxidation-resistant, surgical grade metals, such as 316 Stainless Steel or titanium, using conventional metal fabrication techniques.

An efficient curette 10 is thus disclosed, having two or more blades 26, and in the embodiments illustrated, four blades 26. Preferably, there are three or more blades 26 to balance or equalize the pressure exerted against the surfaces of the opposing vertebral bodies while the end plate disk material, cartilage and/or bone is curetted. Relative to a spoon-like curette or ring curette, the multiple blades 26 of the various embodiments of the present invention expedite the curetting process.

Furthermore, a curette 10 is disclosed in the various embodiments of the present invention which is especially well-suited for use in minimally invasive spine surgery. The curette 10 of the various embodiments of the present invention can enter the disk space through a small opening and is sized and shaped to efficiently clean out central portions of the disk space upon rotation of the curette 10, with only minimal tilting of the handle 16 of the curette 10. Still further, the curette 10 disclosed in the various embodiments of the present invention is sized and shaped to be capable of cleaning and contacting an adjacent vertebral end-plate uniformly so that it does not remove bone excessively from one of the vertebrae.

It will be appreciated by those skilled in the art that changes could be made to the embodiments described above without departing from the broad inventive concept thereof. It is understood, therefore, that this invention is not limited to the particular embodiments disclosed, but it is intended to cover foreseeable modifications within the spirit and scope of the present invention as defined by the appended claims.

What is claimed is:

1. A multi-blade curette tool for use in spinal surgery comprising:
    an elongated member having a proximal end and a distal end;
    a handle disposed at the proximal end;
    a curette head having the shape of an ellipsoid disposed at the distal end and fixedly connected thereto, the curette head being integral and unitary with the elongated member, the curette head being generally tapered toward both the proximal end and the distal end, a first end of the curette head proximate the distal end being tapered to facilitate distraction and entry into a space between vertebral bodies and a second end of the curette head spaced from the distal end being tapered to facilitate removal of the curette head from the space, the curette head including:
        a convexly-shaped and generally tapered nose portion;
        a convexly-shaped and generally tapered base portion;
        a plurality of blades, each blade being generally rigid, fixed in shape, non-flexible and extending from the base portion to the nose portion and integrally attached along an entire length thereof, and each of the plurality of blades being provided with at least one cutting element having a generally planar outer peripheral surface and at least one sharpened edge extending tangentially to the outer peripheral surface from the first end to the second end of the curette head, at least a portion of each sidewall of each blade extending at an angle of less than 90° from the outer peripheral surface, the at least one cutting element of each blade being configured to remove spinal disk material upon rotation of the curette tool in at least one rotational direction; and
    at least two imaginary planes extending through and including a longitudinal axis of the curette tool and the curette head, each imaginary plane extending radially outwardly from the longitudinal axis, the at least two imaginary planes defining an angle of less than 180° and greater than 0° therebetween, at least one blade of the plurality of blades extending within one of the at least two imaginary planes and at least one other blade of the plurality of blades extending within another one of the at least two imaginary planes; and
    a drive stem coupling the handle to the curette head, wherein the drive stem is fixed with respect to the handle and the curette head.

2. The multi-blade curette tool of claim 1, wherein each of the plurality of blades is an elongated member having a first end supported by the base portion and a second end supported by the nose portion.

3. The multi-blade curette tool of claim 2, wherein each of the plurality of blades generally extends between the base and the nose in a generally arcuate manner in a direction generally along the central longitudinal axis of the curette head.

4. The multi-blade curette tool of claim 1, wherein the plurality of blades includes at least three blades.

5. The multi-blade curette tool of claim 1, wherein a maximum length of the curette head, as measured from the nose portion to the base portion along the imaginary central longitudinal plane, is greater than a maximum diameter of the head.

6. The multi-blade curette tool of claim 1, wherein each imaginary plane divides each of the nose portion and the base portion into two generally equal halves.

7. The multi-blade curette tool of claim 1, wherein, in combination, the plurality of blades are sized, shaped and spaced to equalize the pressure exerted against surfaces of opposing vertebral bodies while end plate disk material, cartilage or bone is curetted.

8. A multi-blade curette tool for use in spinal surgery comprising:
   an elongated member having a proximal end and a distal end;
   a handle disposed at the proximal end;
   a curette head having the shape of an ellipsoid disposed at the distal end, the curette head being generally tapered toward the proximal end and the distal end, the curette head including:
      a convexly-shaped and generally tapered nose portion;
      a convexly-shaped and generally tapered base portion;
      a completely solid central core;
      a plurality of blades, each blade being generally rigid, fixed in shape, non-flexible and extending from the base portion to the nose portion, each of the plurality of blades being a continuous member having a first end connected to the base and a second end connected to the nose and an interior portion connected to and extending radially from the central core, and each of the plurality of blades being provided with at least one cutting element having a generally planar outer peripheral surface and at least one sharpened edge extending tangentially to the outer peripheral surface from the first end to the second end of the curette head, at least a portion of each sidewall of each blade extending at an angle of less than 90° from the outer peripheral surface, the at least one cutting element of each blade being configured to remove spinal disk material upon rotation of the curette tool in at least one rotational direction; and
   at least two imaginary planes extending through and including a longitudinal axis of the curette tool and the curette head, each imaginary plane extending radially outwardly from the longitudinal axis, the at least two imaginary planes defining an angle of less than 180° and greater than 0° therebetween, at least one blade of the plurality of blades extending within one of the at least two imaginary planes and at least one other blade of the plurality of blades extending within another one of the at least two imaginary planes; and
   a drive stem coupling the handle to the curette head.

9. The multi-blade curette tool of claim 8, wherein a first end of the curette head proximate the distal end is tapered to facilitate distraction and entry into a space between vertebral bodies and a second end of the curette head spaced from the distal end is tapered to facilitate removal of the curette head from the space.

10. The multi-blade curette tool of claim 9, wherein a maximum length of the curette head, as measured from the nose portion to the base portion along the imaginary central longitudinal plane, is greater than a maximum diameter of the head.

11. The multi-blade curette tool of claim 10, wherein, in combination, the plurality of blades are sized, shaped and spaced to equalize the pressure exerted against surfaces of opposing vertebral bodies while end plate disk material, cartilage or bone is curetted.

12. The multi-blade curette tool of claim 11, wherein each imaginary plane divides each of the nose portion and the base portion into two generally equal halves.

* * * * *